United States Patent
Hunter et al.

(10) Patent No.: US 8,862,630 B2
(45) Date of Patent: Oct. 14, 2014

(54) METHOD AND SYSTEM FOR THE USE OF GEOSPATIAL DATA IN THE DEVELOPMENT, PRODUCTION, AND SALE OF AGRICULTURAL SEED

(75) Inventors: James L. Hunter, Littleton, CO (US);
Steven J. Corak, Raleigh, NC (US);
Steven Langton, Janesville, WI (US);
David K. Langer, Urbandale, IA (US);
Mark W. Spicer, Ankeny, IA (US)

(73) Assignee: Pioneer Hi-Bred International Inc, Johnston, IA (US)

( * ) Notice: Subject to any disclaimer, the term of this patent is extended or adjusted under 35 U.S.C. 154(b) by 379 days.

(21) Appl. No.: 12/793,437

(22) Filed: Jun. 3, 2010

(65) Prior Publication Data

US 2011/0113030 A1    May 12, 2011

Related U.S. Application Data

(60) Provisional application No. 61/183,627, filed on Jun. 3, 2009.

(51) Int. Cl.
| | |
|---|---|
| G06F 17/30 | (2006.01) |
| G06F 7/00 | (2006.01) |
| G06Q 10/00 | (2012.01) |
| C12N 15/82 | (2006.01) |
| G06F 19/12 | (2011.01) |
| A01H 5/10 | (2006.01) |
| G06F 19/28 | (2011.01) |
| G06Q 30/02 | (2012.01) |
| G06Q 50/02 | (2012.01) |

(52) U.S. Cl.
CPC ............ *G06Q 10/00* (2013.01); *C12N 15/8216* (2013.01); *G06F 19/12* (2013.01); *A01H 5/10* (2013.01); *G06F 19/28* (2013.01); *C12N 15/8222* (2013.01); *C12N 15/8261* (2013.01); *G06Q 30/02* (2013.01); *G06Q 50/02* (2013.01)
USPC .......................................................... 707/802

(58) Field of Classification Search
CPC ........... A23V 2002/00; A23V 2300/21; A23V 2250/1862; A23V 2250/187; A23V 2250/1872; A23V 2250/1874; A23V 2250/188; A23V 2250/1886; A01C 1/06; A01H 1/04; G06Q 40/00; G06Q 40/02; G06Q 10/06; G06F 2219/10
USPC .......................................................... 707/802
See application file for complete search history.

(56) References Cited

U.S. PATENT DOCUMENTS

| | | | |
|---|---|---|---|
| 6,359,199 B1 * | 3/2002 | Sun ............................... | 800/320 |
| 6,691,135 B2 | 2/2004 | Pickett et al. | |

(Continued)

OTHER PUBLICATIONS

The Seed Industry in U.S. Agriculture / AIB-786, USDA, Jan. 2004.*

(Continued)

*Primary Examiner* — Kuen Lu
(74) *Attorney, Agent, or Firm* — Pioner Hi-Bred Intl. Inc.

(57) ABSTRACT

A system for aggregating data obtained from different organizations within a seed company or within multiple seed companies is provided. The system may receive seed product development data from a seed product development source, seed production data from a seed production source, and/or seed sales and/or marketing data from a seed sales and/or marketing source. The data may be aggregated in a central storage unit based on the geospatial data associated with the received data. The aggregated data may then be accessed and/or output in response to a query and/or algorithm.

23 Claims, 13 Drawing Sheets

(56) References Cited

U.S. PATENT DOCUMENTS

| | | |
|---|---|---|
| 7,107,285 B2 | 9/2006 | Von Kaenel et al. |
| 2002/0026659 A1* | 2/2002 | Blowers et al. ............... 800/298 |
| 2002/0059091 A1 | 5/2002 | Hay et al. |
| 2005/0050796 A1 | 3/2005 | Wilkin, Jr. |
| 2005/0283314 A1 | 12/2005 | Hall |
| 2006/0104904 A1* | 5/2006 | Lefko et al. .................... 424/9.2 |
| 2006/0282467 A1 | 12/2006 | Peterson et al. |
| 2006/0293913 A1 | 12/2006 | Iwig et al. |

OTHER PUBLICATIONS

"Integrating Seed Systems for Annual Food Crops", Proceedings of a Workshop Held in Malang, Indonesia Oct. 24-27, 1995.*

U.S. Appl. No. 12/558,062, filed Sep. 11, 2009, Daniel Goldman et al.

* cited by examiner

SOURCES

- HYBRID OR VARIETY — 802
- CURRENT LOCATION — 804
  - JOHNSTON, IOWA
- LOCATION LIMITATIONS — 806
  - WITHIN 100 MILES
- 808:
  - ☐ IN FIELD
  - ☐ IN FIELD PREVIOUS YEAR
  - ☐ IN STORAGE

| LOCATION | QUANTITY | SOURCE | TYPE |
|---|---|---|---|
| JOHNSTON, IOWA | 160 ACRES | SMITH FARMS | IN FIELD |
| INDIANOLA, IOWA | 150,000 BUSHELS | JONES FARMS | IN STORAGE |

METHOD AND SYSTEM FOR THE USE OF GEOSPATIAL DATA IN THE DEVELOPMENT, PRODUCTION, AND SALE OF AGRICULTURAL SEED

CROSS-REFERENCE TO RELATED APPLICATIONS

This application claims the benefit of U.S. Provisional Application Ser. No. 61/183,627 filed Jun. 3, 2009 which is incorporated herein by reference in its entirety.

BACKGROUND

Geospatial data is becoming increasingly used in a variety of contexts associated with agriculture. For example, an agricultural biotechnology company or life sciences company may have many different business units which each collect geospatial data for various purposes. In addition, such an organization may collect other types of data which may not include geospatial data. Of course, other types of agriculture companies or other organizations may also collect such data, including those providing agricultural equipment, consulting, or information technology services.

In the context of a plant science or seed company, geospatial data may be collected to support a wide variety of business functions such as research, seed testing, seed production, and sales/marketing. In the research environment, it is often necessary or desirable to individually identify each plant within a research plot. Research plot location is identified by X, Y coordinates. The location of a plant within the plot can be thought of the Z axis or plant sequence number. In other words, the third plant in plot 110, 50. In hill plots or research schemes where the unit of interest is a single plant when a plant's location can be defined as an X, Y coordinate. One approach has been to define plant or plot location using a relative coordinate system that expresses location with respect to the first planted plot's location. Thus each plot was defined by plot or row number associated with a first axis (X axis) and a range number associated with a second axis (Y axis), the second axis perpendicular to the first axis. Thus each plant could be individually identified. This approach relies on the use of labeled stakes or plant tags to indicate the location of plots. The location of a plot or research experiment with respect to other plots or with surrounding fields was either undefined, or defined logically (difference in coordinates), or generally in terms of separation distance using manual means of establishing the distance from the edge of two experiments or parcels of land.

With such an approach, the creation of an actual physical map, if needed, showing the spatial relationships between an experiment and surrounding experiments or fields, would rely upon the manual preparation of a map. Such maps are not highly precise and may not always permit effective documentation of absolute distances required for regulatory compliance.

Research processes typically employ logical maps that show the positional relationship between one experiment and another and one plot with another. These maps do not describe actual physical location, i.e. longitude and latitude. They also fail to provide a means of accurately establishing distance from one plot to another or from one plot to regions of surrounding fields.

In the past, measuring wheels or tape measures were utilized to determine the distance between selected points and adjacent fields or experiments. These measurements provided relative distances, but were typically not able to establish absolute position because of the absence of a fixed and defined reference point. These measurements were of limited value for supporting downstream research processes because they were limited in number and not readily available for use in other applications or processes.

Thus, field research activities rely on tags or stakes to label plants, plots, or rows. To reduce labor it is common to label only selected plots or plants. During the various field activities it is possible to have a plot erroneously identified. This error is not readily detected. With the advent of molecular techniques for inserting novel genes into plants field research activities have become increasingly subject to regulatory requirements for planting at defined locations with adherence to business rules or regulatory requirements for genetic (pollen) isolation from non-regulated plants or fields. This isolation requirement is important for ensuring the containment of pollen that may serve as a source of "genetic contamination." Manual methods for making and utilizing measurements preclude their widespread use in supporting research processes such as: planning; planting; stand counting; thinning; spectral or physiological characterization; tissue sampling; and harvest validation.

Research is merely one aspect associated with a seed business or life sciences company. Another aspect is production where plants are grown to provide sufficient seeds for commercialization. As previously mentioned, geospatial data associated with seed production activities may be collected by a seed company.

There are numerous problems associated with production. These include the isolation requirements discussed above with respect to research and other problems associated with identifying fields for use in production. In addition to these problems associated with production, there are also the problems that occur when production falls short, such as the problem of identifying potential alternative sources of seed, such as from a producer growing a particular hybrid or variety. In addition, to the problems associated with research and production, there are also problems associated with the marketing or sale of seed products. In particular, in the course of marketing or selling seed products, producers (customers) will often seek recommendations regarding which seed to plant on which fields. There is a desire to provide the best recommendations possible in order to satisfy customers. As previously mentioned, there may be geospatial data available to a seed company which is associated with sales and marketing, such as data acquired from demonstration plots or a producer.

What is needed is to provide geospatial data from multiple sources and to combine the data in order to increase the value and use of the data in activities such as, but not limited to seed research, product development, crop management, regulatory testing, regulatory approval, seed quality management, regulatory compliance, seed production, and related sales activities.

SUMMARY

Geospatial data may be used to provide a shared or common geospatial context within which different business functions may operate in order to provide increased efficiencies or synergies. By aggregating data from different business sources such as, but not limited to, research or product development, seed production, and sales and/or marketing, the data may be leveraged to enable the use of decision making or process optimization tools. In addition, data may be added from other data sources, such as, but not limited to, weather data sources, government data sources, or other data sources to further enable the use of decision making or process optimization tools.

According to one aspect, a system for using geospatial data to link agricultural business functions and/or processes is provided. The system includes a system and a plurality of data sources. Each of the plurality of data sources is accessible by the computing system and is associated with at least one agricultural business function or process. Further, in the plurality of data sources, at least one data source comprises or is associated with geospatial data. The computing system is adapted to access the plurality of data sources and, using the geospatial data, to identify any data relevant to a decision associated with an agricultural function and/or process, identify any data relevant to biological functions or processes relevant to a decision or analysis.

According to another aspect a method is provided for geospatial data management. The method includes providing a plurality of data sources, accessing data from the plurality of data sources, and using geospatial data to identify any subset of data relevant for an analysis and/or decision supporting an agricultural business function and/or process. The data sources include but are not limited to geospatial data, seed product data, seed product development data, seed production data, crop management data, sales or marketing data, field data, environmental data, biological data, and the like.

Agricultural business functions and processes include plant research activities and processes. According to another aspect, a method for using geospatial data in a plant research activity or process is provided. The method includes using geospatial data to define field boundaries for a research field or plot, developing a planting plan using the geospatial data, implementing the planting plan using the geospatial data, collecting data about the plants using the geospatial data, and storing the collected data and at least a portion of the geospatial data in a data source. Optionally, the planting plan may include crop management plans, and/or data collection plans. In some examples the collected data includes one or more of the field boundaries, planting plan, and/or implementation information.

According to one aspect, a system for aggregating seed product development data and seed production data may be provided. The system may include a computing system, such as a processor and computing memory for storing instructions that may be executed by the processor. Seed product development data may be received from a seed product development source. The seed product development data may comprise geospatial information associated with a seed product, a land unit, or both a seed product and a land unit used for seed product development. Additionally, seed production data may be received from a seed production source. The seed production data may comprise geospatial information associated with a seed product, a land unit, or both a seed product and a land unit used for seed product development. The seed product development data and the seed production data may be aggregated based on their respective geospatial information and output data may be sent in response to a query based on the aggregated data.

According to another aspect a method is provided for aggregating seed product development data and seed production data. The method includes receiving seed product development data from a seed product development source. The seed product development data may comprise geospatial information associated with a seed product, a land unit, or both a seed product and a land unit used for seed product development. Additionally, seed production data may be received from a seed production source, wherein the seed production data comprises geospatial information associated with a seed product, a land unit, or both a seed product and a land unit used for seed production. The seed product development data and the seed production data may be aggregated based on the respective geospatial information and output data may be sent in response to a query and based on said aggregating.

According to another aspect, a method for aggregating data from a plurality of sources is provided. The method includes receiving data from a plurality of sources. The data received from each source comprises geospatial information associated with a seed product, a land unit, or both a seed product and a land unit. Additionally, each source of the plurality of sources is associated with a different business function. The data received from the plurality of sources is aggregated based on the geospatial information associated with the data and output data is sent in response to a query and based on said aggregating.

By having geospatial data collected by or for different business units available for use across an enterprise synergies may be created as data collected for one purpose by one business unit may be used by a different business unit for a different purpose. This ability to access the additional data assists in addressing problems encountered by various business units, including research and development, production, and sales and marketing.

BRIEF DESCRIPTION OF THE DRAWINGS

FIG. 8 is a screen display of a tool that can be used for sourcing commercial grain.

DETAILED DESCRIPTION

I. Overview

Figure 1:
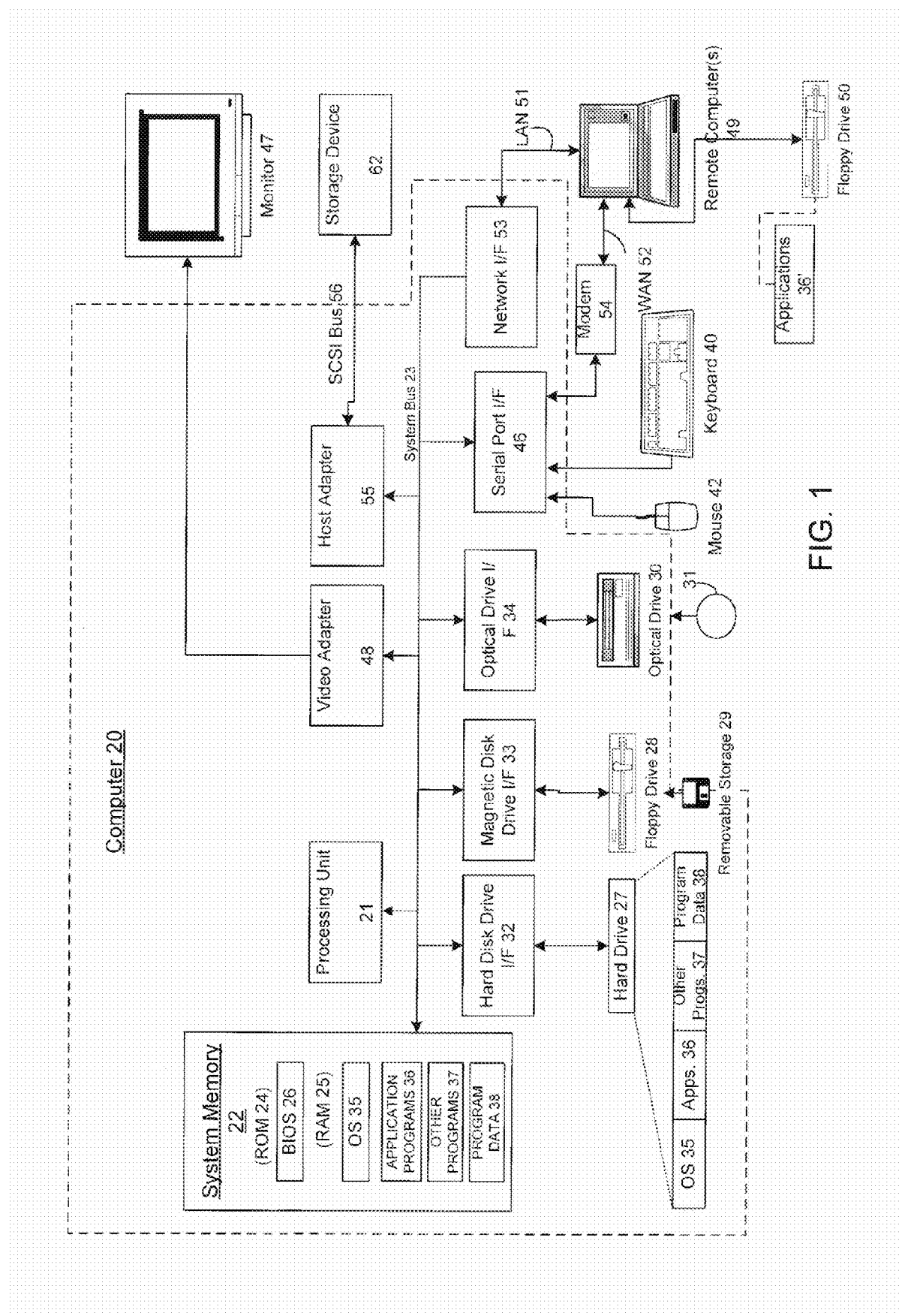
FIG. 1 is a block diagram representing a computer system in which aspects of the present invention may be incorporated.

A plant science or seed company may be engaged in the business of providing seed. For example, aspects of the business may include research, seed testing, product development, seed production, and/or sales and marketing. The research aspect of such a business may involve activities such as plant breeding, plant transformation, gene testing, mapping populations, marker development, and/or related activities for example. As a part of the research activities, research experiments may be performed which may involve growing seed so as to allow for the collection of data at different stages of development of the resulting plants. The research activities may enable new product development or product improvements.

The seed production organization of a seed company may encompass different aspects of the business. For example, the seed production aspects of such a business may involve activities directed towards producing sufficient quantities of commercial seed for sale. To do so, the seed production organization of a seed company may grow desired plants in fields that may be owned and/or controlled by the business. Alternatively, the business may contract production fields from others, or potentially even buy grain for use as seed.

The sales and/or marketing organizations of a seed company may encompass yet another aspect of the business. For example, the sales and/or marketing organizations may have "demo" plots where multiple products may be planted beside each other in strips which may make it easy to compare potential products. There may also be many strip plots where a farmer may be given a seed of a new product or pre-commercial variety for planting in their field. The farmer may then harvest the strip plot(s) and get a yield value. In some examples, an adjacent area may be harvested of a different genotype for comparison's sake. A sales and/or marketing use for geospatial data in this context may be to allow a customer to see where a product of interest may be included in a demo plot or in a strip plot within a defined distance of their farm. The sales and/or marketing organization may also use the geospatial data to summarize how a product or pre-commercial variety may have performed in comparison to alternative products. A farmer may be familiar with a plot location and may value the comparison more by knowing the environment in which these plots grew and/or how the plot(s) and/or crop(s) were likely managed.

Another aspect of the sales and/or marketing organization of a seed company may be to provide for the sale of seed. A number of activities may support that goal. The activities may include growing demonstration plots, site visits, tours, providing associated services to producers (also referred to as "growers" or "customers") which may help the producers select which seed products to use and/or provide related agronomic services which may make recommendations regarding product placement or management practices which may be used with the seed products.

As illustrated above, a seed company may have multiple organizations and/or within the company that collect various types of data related to research, seed testing, product development, seed production, and/or sales and marketing or the like. The various types of data may include but are not limited to historical and/or current information about land units, plots, field boundaries, field maps, weather, environment, planting plans, crop management practices, plant development, genotype, pedigree, field conditions, phenotype, governmental or regulatory requirements, geospatial data, and/or the like. The data collected from the different organizations within the company may be aggregated in a central location to assist in making the data more readily available, to control data management, to assess and manage data quality, to leverage and/or expand the data from various independent test to produce meta-data or meta-studies, to improve data set size or quality for product development, testing processes, and/or decisions within and between groups and functions in the company. For example, the data may be aggregated in a central storage unit, such as a server computer for example, so that data collected from each organization within the company may be accessed. The data may be accessed by organizations within the company, sub-organizations within the company, or organizations and/or sub-organizations within multiple companies or the like.

Aggregating data from various sources and the other embodiments described herein may be executed on a computer. FIG. 1 and the following discussion are intended to provide a brief general description of a suitable computing environment in which the embodiments described herein may be implemented. Although not required, the described embodiments may be implemented in the general context of computer executable instructions being executed by a computing device, such as a client workstation or a server for example. Those skilled in the art will appreciate that the embodiments described herein may be practiced with other computer system configurations, including hand held devices, such as cellular phones, smart phones, PDAs, or the like, multi processor systems, microprocessor based or programmable consumer electronics, network PCs, minicomputers, mainframe computers, or the like. The embodiments described herein may also be practiced in distributed computing environments where tasks are performed by remote processing devices that are linked through a communications network.

Referring now to FIG. 1, an exemplary general purpose computing system is depicted. The general purpose computing system may include a conventional computer 20 or the like, including at least one processor or processing unit 21, a system memory 22, and a system bus 23 that communicatively couples various system components including the system memory to the processing unit 21 when the system is in an operational state. The system bus 23 may be any of several types of bus structures including a memory bus or memory controller, a peripheral bus, and a local bus using any of a variety of bus architectures. The system memory may include read only memory (ROM) 24 and random access memory (RAM) 25. A basic input/output system 26 (BIOS), containing the basic routines that help to transfer information between elements within the computer 20, such as during start up, is stored in ROM 24. The computer 20 may further include a hard disk drive 27 for reading from and writing to a hard disk (not shown), a magnetic disk drive 28 for reading from or writing to a removable magnetic disk 29, and an optical disk drive 30 for reading from or writing to a removable optical disk 31 such as a CD ROM or other optical media. The hard disk drive 27, magnetic disk drive 28, and optical disk drive 30 are shown as connected to the system bus 23 by a hard disk drive interface 32, a magnetic disk drive interface 33, and an optical drive interface 34, respectively. The drives and their associated computer readable media provide non volatile storage of computer readable instructions, data structures, program modules and other data for the computer 20. Although the exemplary environment described herein employs a hard disk, a removable magnetic disk 29 and a removable optical disk 31, it should be appreciated by those skilled in the art that other types of computer readable media which can store data that is accessible by a computer, such as flash memory cards, digital video disks, random access memories (RAMs), read only memories (ROMs) and the like may also be used in the exemplary operating environment. Generally, such computer readable storage media can be used in some embodiments to store processor executable instructions embodying aspects of the present disclosure.

A number of program modules comprising computer-readable instructions may be stored on computer-readable media such as the hard disk, magnetic disk 29, optical disk 31, ROM 24 or RAM 25, including an operating system 35, one or more application programs 36, other program modules 37 and program data 38. Upon execution by the processing unit, the computer-readable instructions cause the actions described in more detail below to be carried out. A user may enter commands and information into the computer 20 through input devices such as a keyboard 40 and/or pointing device 42. These and other input devices may be connected to the processing unit 21 through a serial port interface 46 that is coupled to the system bus, but may be connected by other interfaces, such as a parallel port, game port or universal serial bus (USB). A display 47 or other type of display device can also be connected to the system bus 23 via an interface, such as a video adapter 48. In addition to the display 47, computers typically include other peripheral output devices (not shown), such as speakers and printers. The exemplary system of FIG. 1 also includes a host adapter 55, Small Computer System Interface (SCSI) bus 56, and an external storage device 62 connected to the SCSI bus 56.

Additionally, the computer 20 may operate in a networked environment using logical connections to one or more remote computers, such as a remote computer 49. The remote computer 49 may be another computer, a server, a router, a network PC, a peer device or other common network node, and typically can include many or all of the elements described above relative to the computer 20, although only a memory storage device 50 has been illustrated in FIG. 1. The logical connections depicted in FIG. 1 may include a local area network (LAN) 51 and a wide area network (WAN) 52. Such networking environments may be commonplace in offices, enterprise wide computer networks, intranets and the Internet.

When used in a LAN networking environment, the computer 20 may be connected to the LAN 51 through a network interface or adapter 53. When used in a WAN networking environment, the computer 20 can typically include a modem 54 or other means for establishing communications over the wide area network 52, such as the Internet. The modem 54, which may be internal or external, can be connected to the system bus 23 via the serial port interface 46. In a networked environment, program modules depicted relative to the computer 20, or portions thereof, may be stored in the remote memory storage device. It will be appreciated that the network connections shown are exemplary and other means of establishing a communications link between the computers may be used. Moreover, while it is envisioned that numerous embodiments of the present disclosure are particularly well-suited for computerized systems, nothing in this document is intended to limit the disclosure to such embodiments.

Figure 2:
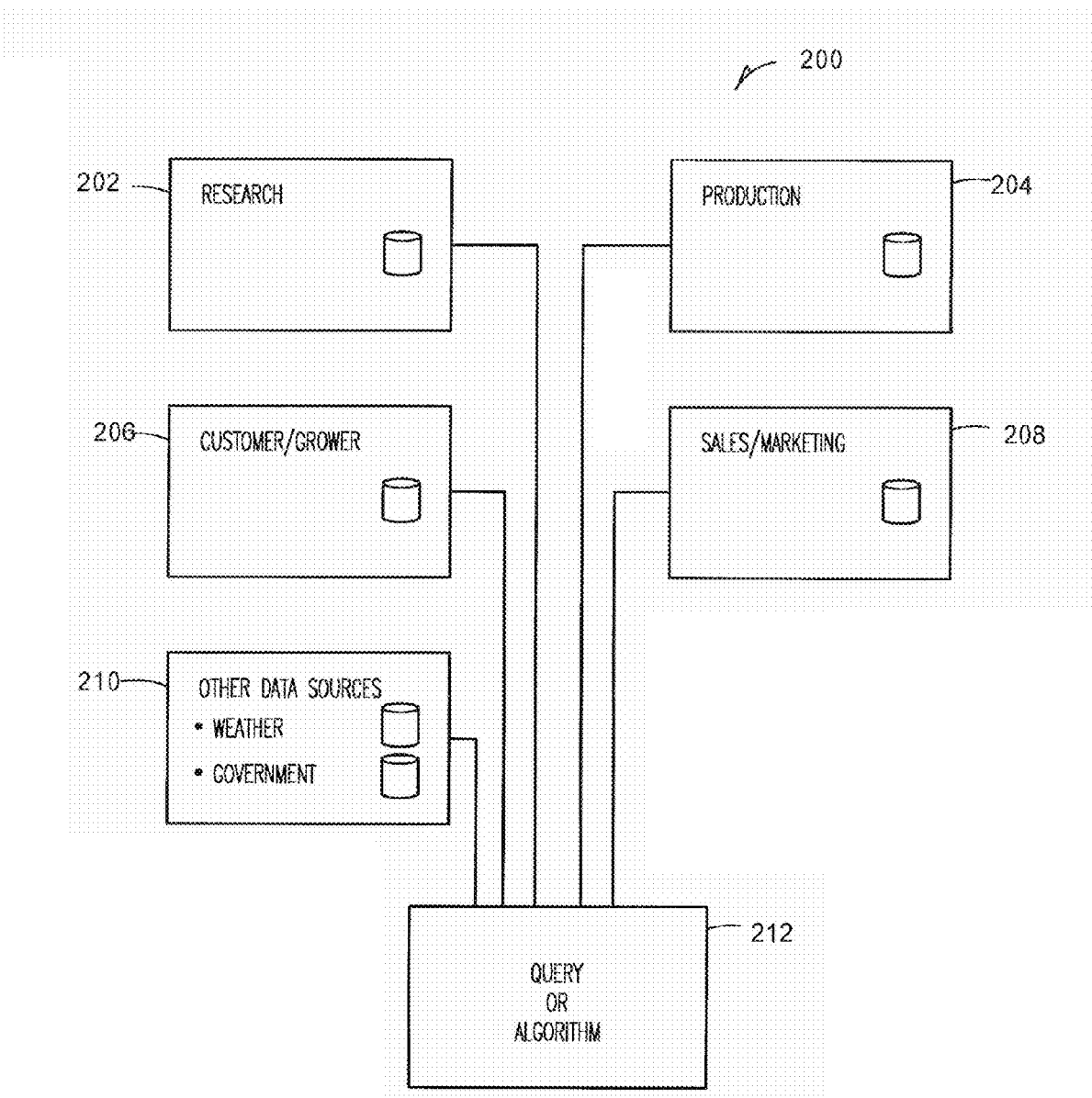
FIG. 2 is a block diagram of a query or algorithm associated with a computing system accessing data from diverse data sources.

FIG. 2 illustrates one example of a system 200 that may be executed on a computing system. In the system 200, a query or algorithm 212 may be executed on the computing system and may be used to find relevant data that may be present in any of a centralized database, a data store, or in a plurality of different data sources. Each data source may be one or more separate databases, one or more tables within a database, one or more computer accessible files, or other types of data sources. Additionally, each data source may be located in a separate organization, sub-organization, company, or the like. The data may be sent and/or accessed via a local source or a remote source which may be linked through a communications network or the like. For example, each source may be a local source such as a local client computer or local server computer. According to one example, a local client computer or a local server computer may be a computer located within a company or within a business organization from which the data is being sent and/or accessed. Alternatively, a remote source may be a remote client computer or a remote server computer at a location associated with another company or at a location associated with another business organization from where the data is being sent and/or accessed for example. When data is being sent and/or accessed, either locally or remotely for example, security, access, authentication, and/or permission requirements may be used. For example, when data may be sent and/or accessed from a remote computer system, a remote computer system authentication or a user authentication may be required before receipt and/or access to the data may be granted.

As the data may be received from multiple different sources, the data may be aggregated by system 200. The query or algorithm 212 may access one or more of a research data source 202, a customer or grower data source 206, a production data source 204, a sales or marketing data source 208, as well as one or more other data sources 210. Examples of other types of data sources 210 may include government databases, meteorological or weather databases, mapping databases, or other types of information that may be of interest. The data received from each data source may be geospatial object data, geospatial attribute data, or non-geospatial data for example. Geospatial object data may be a field, a road, a river, or the like. The geospatial object data received from a data source may describe the size, shape, and/or position of the geospatial object for example. Geospatial attribute data may be a location of or geospatial context for a piece of data or information. For example, geospatial attribute data for a grain bin may include the grain bin's latitude and longitude, capacity, current contents, ownership, and/or other information related to the grain bin. Non-geospatial data may include data such as the non-geospatial data described herein. The query or algorithm 212, in accessing multiple data sources may use geospatial information to find and/or use data that may be relevant or of interest. For example, the query or algorithm 212 may access seed product and/or land unit data that may be indexed according to geospatial information associated with the seed product and/or land unit data. The query or algorithm 212 may also access seed product and/or land data that may be indexed according to non-geospatial information, such as hybrid seed type, crop type, owner information, permanent field information, current field information, or any other non-geospatial information as described herein. The information identified by the query or algorithm 212 may be used to give a geospatial context to the non-geospatial data received from a source.

A problem associated with a life sciences or seed production organization may be the variability associated with biological processes. The variability associated with biological processes may affect research activities, seed production, as well as crop production. The query or algorithm 212 may be used to identify information associated with a particular location or area, such as a field for example, as well as surrounding areas, such as an adjacent field. For example, the information identified by the query or algorithm 212 may be used to provide information to prevent genetic contamination. For example, transgenic and/or pure seed data may be identified and a determination may be made as to other contaminating or potentially contaminating transgenic and/or pure seed locations or areas. The information identified by the query or algorithm 212 may be used to provide additional insight into data, for example, data received from another source, connections between data from two separate sources, possible impact of use of a first land unit on the use of a second land unit and the like. For example, outputted data may indicate a potential interaction, such as contamination, between a transgenic seed in development and a seed in production.

Figure 3:
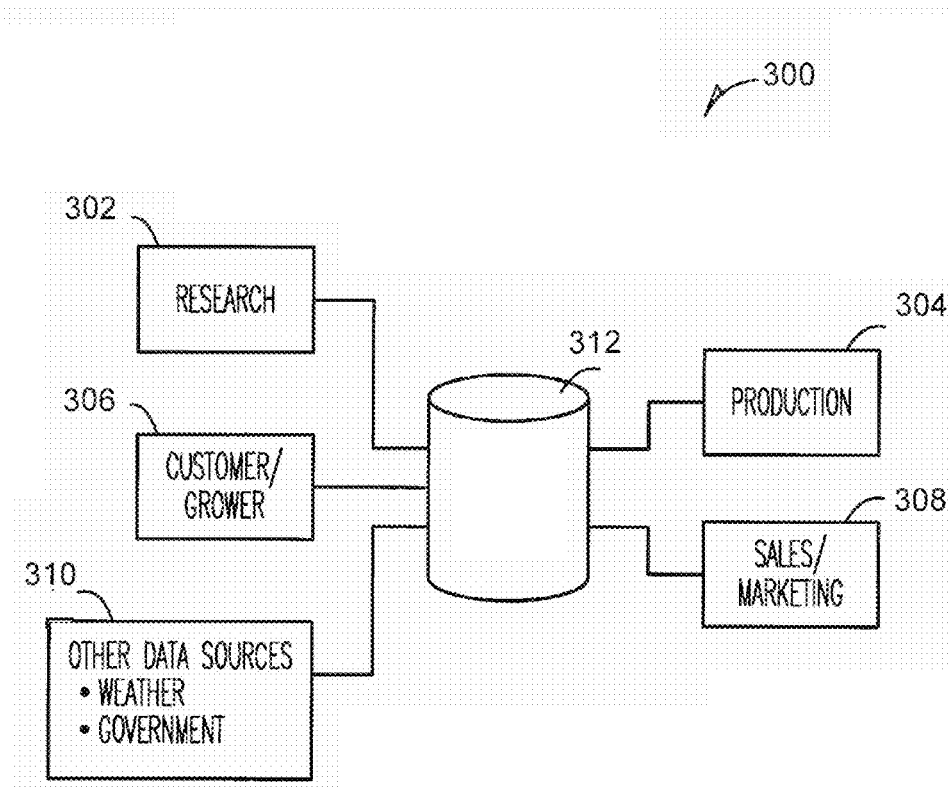
FIG. 3 is a block diagram showing a database accessible to different business units of an enterprise.
Figure 5:
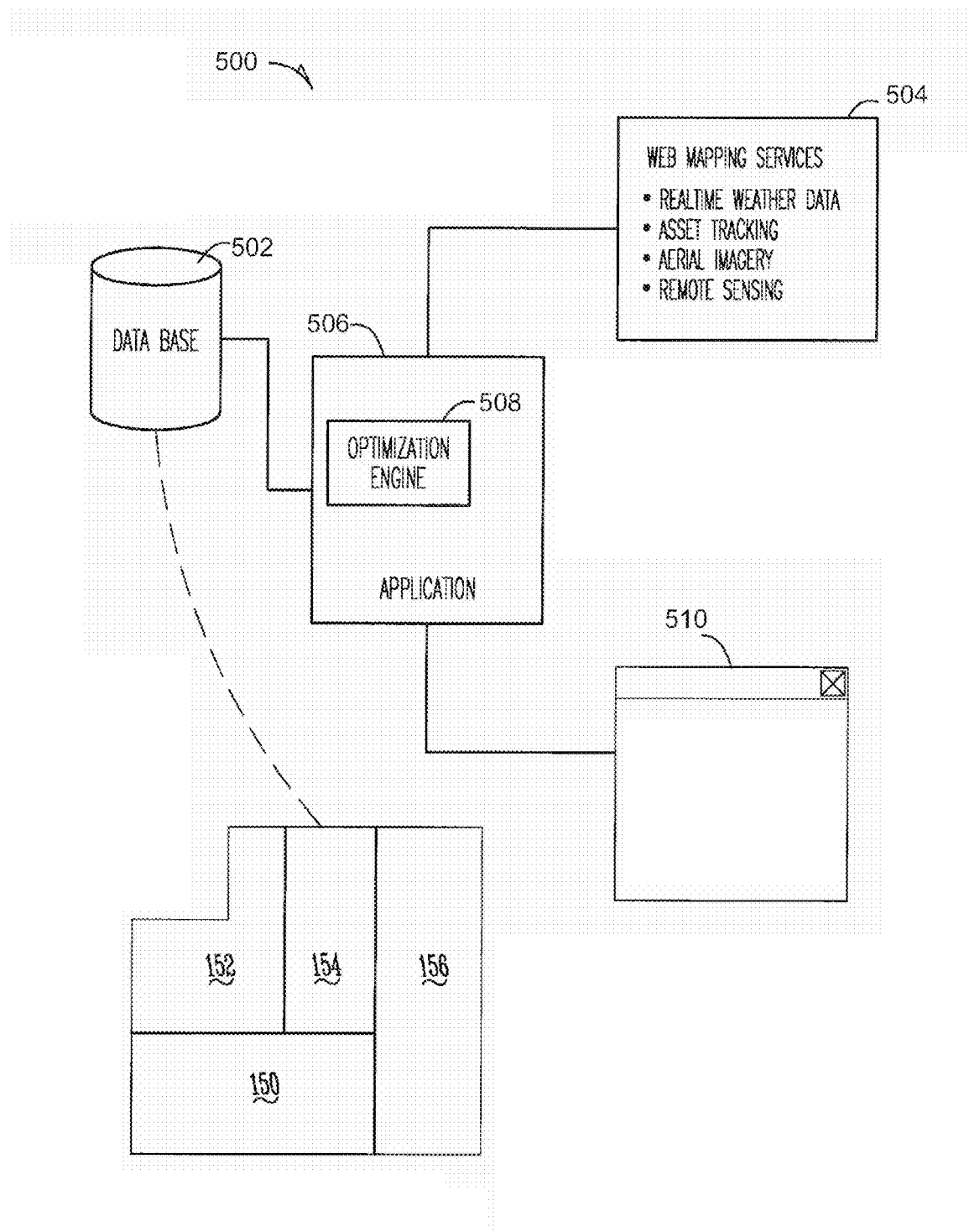
FIG. 5 is a pictorial representation of a system for using geo-referenced data.

In FIG. 2, the query or algorithm 212 may pull data from the various data sources. In FIG. 3, data from various sources is aggregated in a data store 312. The various sources of data may include, without limitation: a research data 302, customer or grower data 306, production data 304, sales and/or marketing data 308, and/or other data sources 310, which may include weather data sources, government data sources or other types of data sources. Thus, as shown in FIG. 3, data from varying types of data sources may be aggregated together into a central data store location. FIG. 5 is pictorial representation of a system for using a database which may include geospatial data. The system 500 includes an application 506. The application 506 may be in operative communication with a database 502 which may include geospatial data. The database 502 may include any type of additional data which may or may not be directly associated with the geospatial data. Although described as a single database 502 in this example, it is to be understood that instead of a single database 502 any number of diverse types of data sources may be used as described herein. The database 502 and the application 506 may be accessed through a network. For example, the application 506 may be accessed over a network using a web-based interface 510. In addition, the application 506 may be in operative communication with web mapping services 504 for providing data such as weather data, asset tracking, aerial imagery, and remote sensing. The database 502 may also link geospatial data to fields or land boundaries. Fields 150, 152, 154, and 156 are shown as examples of fields or land units for which geospatial data may be provided in the database 502.

Figure 6:
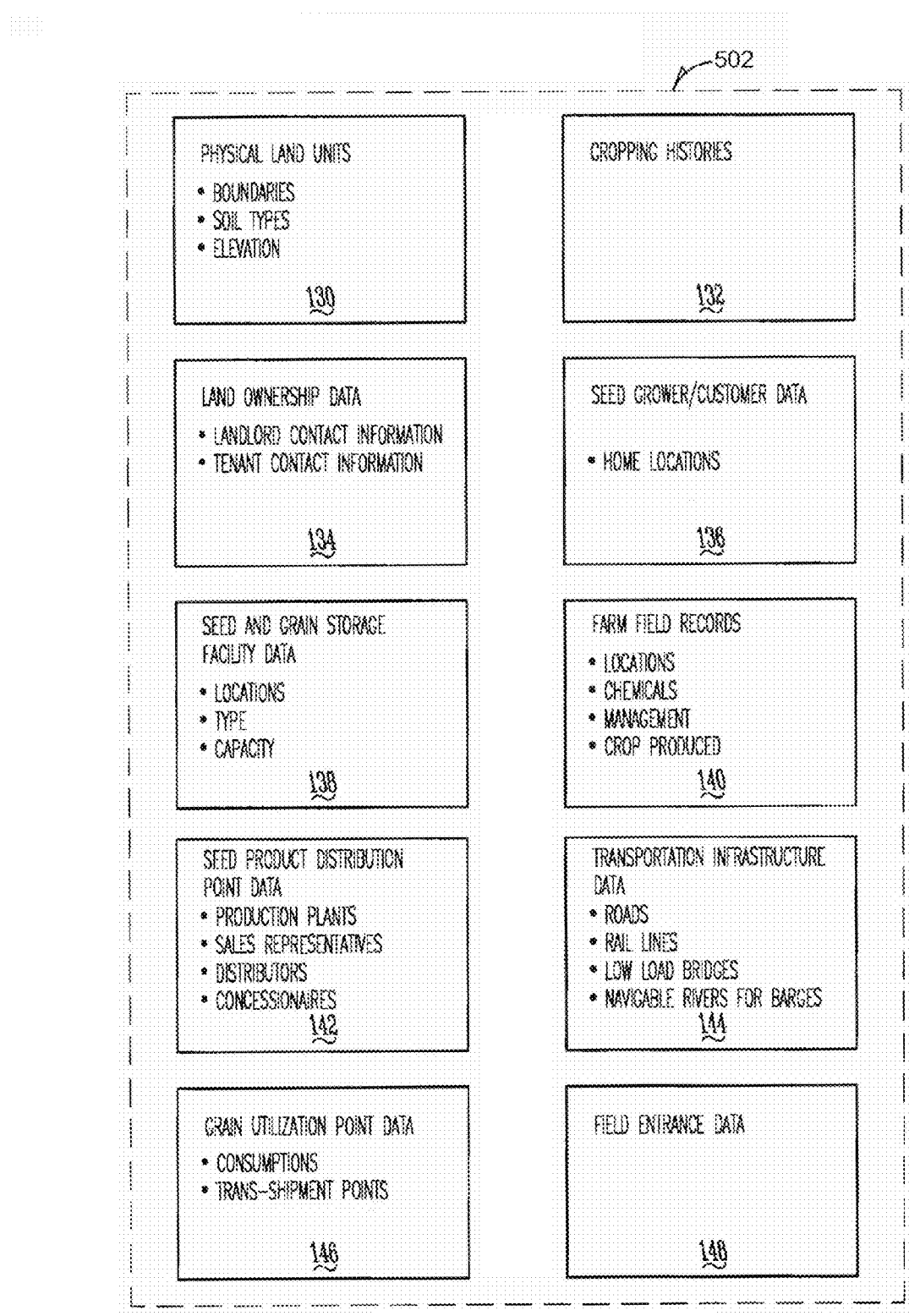
FIG. 6 illustrates a database containing geo-referenced data.

FIG. 6 illustrates the database 502, showing an example of different types of data which may be collected and used. The different types of data in database 502 may be associated with geospatial data for reference, aggregation, and/or use. Database 502 may contain data such as physical land unit data 130, cropping history data 132, land ownership data 134, seed grower and/or customer data 136, seed and grain storage facility data 138, farm field records 140, seed production distribution point data 142, transportation infrastructure data 144, grain utilization point data 146, and/or field entrance data 148 or the like. Physical land unit data 130 may include physical land units, such as fields for example, and associated information such as, but not limited to, plots, boundaries, soil types, elevation, and related information. Cropping history data 132 may include cropping history data collected over one or more periods of time. Cropping history data may be from farmers, customers, research, production, contractors, agronomists, scouts, sales, marketing, suppliers, landlords, and the like. Land ownership data 134 may include land ownership information, such as contact information for any owners, managers, landlords and tenants for example. Seed grower and/or customer data 136 may include seed grower and/or customer names, as well as other relevant information. Seed grower and/or customer data 136 may or may not overlap with land ownership data 134. Seed grower and/or customer data 136 may also include home locations for seed growers and/or customers. Seed and grain storage facility data 138 may include locations and types of seed and grain storage facilities, capacity information, as well as related information. Farm field records 140 may include farm field records from farmers, customers, research, production, contractors, agronomists, scouts, sales, marketing, and/or input suppliers on chemicals applied, crop management practices used, and/or crops produced on a parcel of land. Farm field records may also include information about quantity and quality of crop production. Seed production distribution point data 142 may include data from production plants, sales representatives, distributors, concessionaires, or others. Transportation infrastructure data 144 may include data from roads, rail lines, low load bridges, navigable rivers for barges, and related information. Grain utilization point data 146 may include data about points where grain may be consumed or trans-shipment points. Examples of grain utilization points may include grain processors, ethanol, biodiesel, food, or feed manufacturing facilities. Field entrance data 148 may include data regarding locations of field entrances to particular fields.

In addition to the data shown in FIG. 6, other types of data including production data, research data, sales data, and/or marketing data may be included within the database 502. The aggregation and/or association of different types of data from different sources may allow data collected for one purpose to be used for a different purpose, thereby increasing efficiency within an enterprise or business and also creating opportunities for additional types of analyses.

To assist in explanation, examples of the use of data in different contexts are explained below with respect to different aspects of a business.

II. Research and/or Product Development

Figure 4:
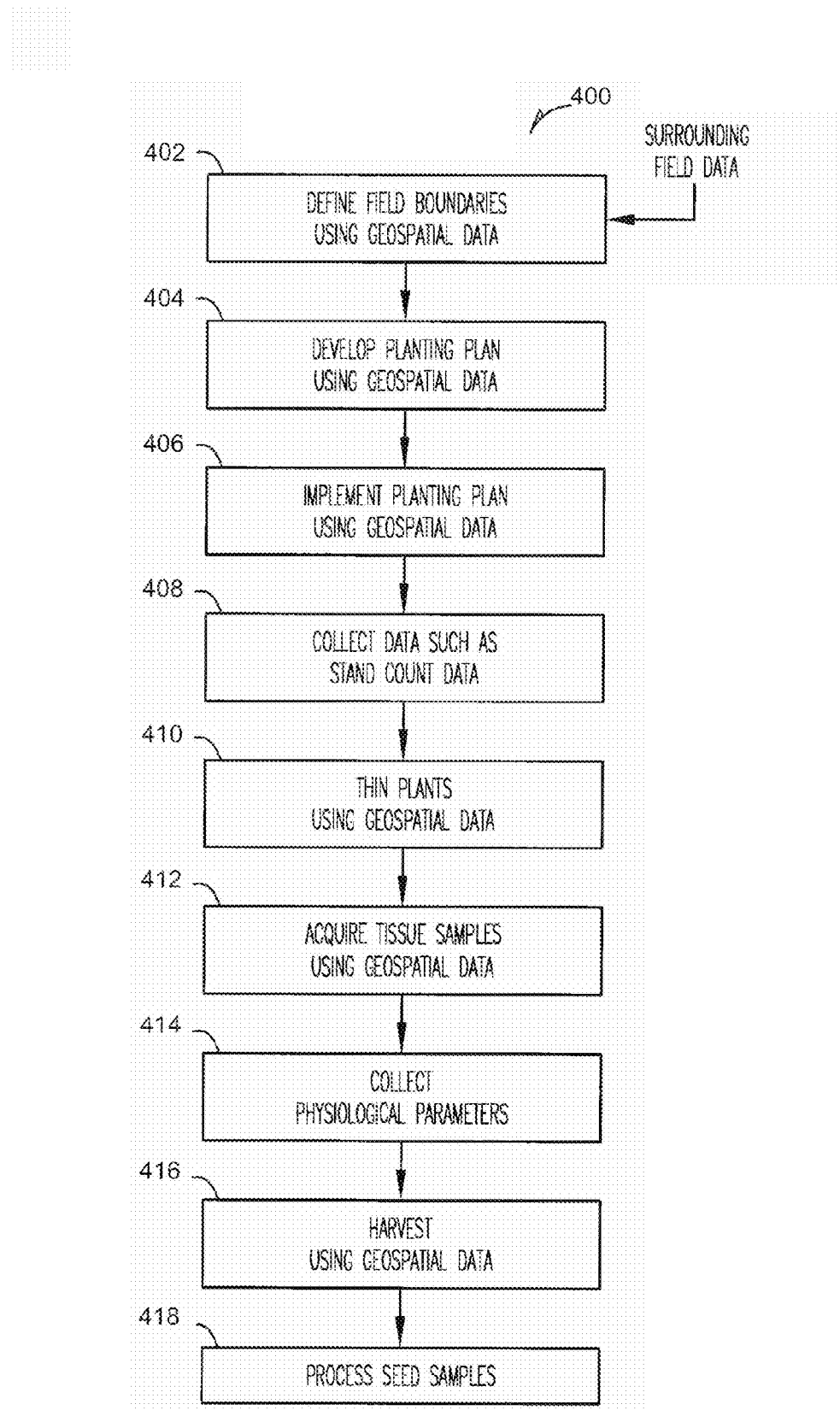
FIG. 4 is a flow diagram of plant research activities where geospatial data is used.

Research experiments may be performed as a part of the research and/or product development process. This may involve growing seed to allow for the collection of data at different stages of development of the resulting plants. Geospatial data may be used in the plant research process. FIG. 4 illustrates one example of a process that may be used in research activities. The process 400 includes a step 402 where field boundaries may be defined using geospatial data. Step 402 may consider various types of information in defining field boundaries including features such as unusable areas such as creeks or obstacles, drainage information, tiling information, and/or data regarding surrounding fields. Next in step 404, a planting plan may be developed using geospatial data. Thus, for example, the geospatial data may be used to specify boundaries of a plot, the position of rows within the plot, or even the position of particular plants. In step 406, the planting plan may be implemented using geospatial data. In step 408, data such as stand count may be collected. In step 410, plants may be thinned using geospatial data. In step 412, tissue samples may be acquired using geospatial data. In step 414, physiological parameters may be collected. In step 416, harvest may be performed using geospatial data. In step 418, seed samples may be processed.

Geospatial data may be used to describe locations associated with research activities. The creation of maps may rely on relative locations, grid systems, or the like. In addition, one may appreciate the benefit of using geospatial data to create maps with absolute locations, described herein. For example, collected geospatial data may allow the creation of maps that describe the planting plan in step 404 that may use absolute position to describe plot, experiment, and field perimeters. This planting plan may permit the assessment of whether the plan complies with regulatory requirements and may also allow the optimization of available field areas. This planning process may start with using a GPS receiver to establish field boundaries within which plots may be established. A computer interface may allow the entry of information about surrounding field or areas that is relevant to establishing compliance with various regulatory requirements.

In step 406, once the planting plan is complete, a GPS equipped planter with associated software may be used to direct equipment operators to initiate planting of the first plot at the desired coordinate position, within some defined tolerance. The planter may plant seed samples and may determine coordinates for the starting and ending position for each plot using a GPS signal and additional sensors such as slippage compensated ground driven encoders for example. Each seed sample's identity may be confirmed prior to planting. At the completion of planting, a digital map may be created showing the absolute location of each plot, the seed contained in each plot, and/or the experiment's and field's perimeter. Isolation lines showing defined distance between a plot, an experiment and/or a field may be readily generated thereby confirming and/or documenting compliance with the planting plan, regulatory isolation requirements, refuge requirements, ISO9000 requirements, company best practices, and the like. Additional data, such as planting density, chemical applications, sampling, soil type, and/or the like may also be associated with these geospatial referenced database records.

Once planted seeds have germinated and emerged, the number and distribution of plants within each plot may be described using GPS and/or sensor technology, such as shown in step 408 for example. Such a system may use one or more sensors to identify the presence of a plant and to characterize its height. Such early stand count data along with information from the planter as to the number of seeds planted may provide a valuable characterization of Stand Establishment. This sensor package in combination with GPS and other spatial sensors may allow estimation of the distance between plants sequentially positioned in a row, and may allow determination of the aggregate number of plants contained within a row or plot whose absolute coordinates were defined during the planting process for example. With stand count data available, each plot's stand may be adjusted to achieve the desired plant number and distribution within each plot. This may be done by manual means or by using an automated system which optionally may be guided by GPS.

An automated system may use data on the location of each plant within each plot, thereby allowing a heuristically driven application that may identify the specific plants to be removed. The automated system may use GPS in conjunction with other sensors to identify target plants and to control actuation of a "cutter" that may sever the target plant at its base. This heuristic thinning application may consider plant height and the distance to adjacent plants to determine the best plants to remove in order to achieve the target stand and plant-to-plant spacing thereby generating the best quality data. This thinning may be performed in step 410.

Tissue samples for analysis as shown in step 412 may be acquired before and/or after the thinning step 410. If acquired before step 410, the results of the analysis of the samples may be used as one criteria to cull plants, for example based on the presence or absence of a transgene or marker. Geospatial technology may be used to help assure that tissue samples are in fact derived from the desired plot and plant. Proper identification may be important because genetic marker and/or analysis data may be used to determine which plants to pollinate or remove from an experiment. Thus it may be important that the correct association is maintained between a plant and samples are derived from the plot.

As the plants develop and the plant canopy fills and/or closes, a variety of physiological parameters may be monitored and used to discriminate between phenotypes as shown in step 414. One technology for this application may be hyper-spectral data gathered by a mobile spectrometer/radiometer. A mobile spectrometer/radiometer device may collect data that should be associated with a specific plot or plant to be useful. The incorporation of GPS and other positioning sensors may allow this data to be correctly associated with the proper plot or plants from which it was generated.

Other data may be recorded whereby a data collection unit may be either held manually or machine-mounted for example. Data may be recorded and the data points may be associated with a plot based on the geospatial position of the data recorder and the physical plot.

Upon maturation, research plots may be harvested in step 416. Research plot harvesters may be equipped with GPS and other sensors that may allow positive confirmation that the harvester is in a specific plot and may allow automatic steering of the harvester. In some cases, only selected plots may be harvested when prior analysis has shown them to contain a superior or desired genotype, and/or a phenotype of interest. Since an accurate map with absolute positional data may be created for each plot at planting, geospatial technology may facilitate the discard of undesirable plots and may assist in ensuring the harvest of desirable plots.

After the harvest and processing of seed samples in step 418, the seed samples may be used to plant successive generations of research plots. If a case of genetic contamination is detected, where traits or characteristics may be conferred by one or more transgenes for example, or a change in regulatory status occurs, the use of geospatial data and technology may provide a means of automating the identification of plots located within a specific distance of a contaminating source of pollen. This may facilitate the "quarantine" of seed samples within the defined distance for testing and/or destruction. If these questionable samples were already used for planting the next generation of plots, geospatial tools may permit their ready location and destruction. The geospatial tools may also support the ready definition of an adjacent "buffer" area that may also be targeted for destruction.

Thus, geospatial information may support a wide range of discrete processes. The availability and use of geospatial data, such as absolute position for example, may allow processes to be automated and errors to be eliminated.

The development of new crop varieties or hybrids involves the establishment and characterization of plants and/or field plots. These plants and/or field plots may be characterized so as to permit the identification of plots or genotypes demonstrating superior phenotypes. The characterization dataset may include observations on a wide range of agronomically significant traits or characteristics, including but not limited to: stand establishment; disease resistance; stalk strength; root lodging; brittle snap resistance; stalk lodging; nitrogen use efficiency; water use efficiency; drought stress tolerance or resistance; seed or grain yield; resistance or tolerance to insect infestation or disease infection; plant height and biomass; tolerance to high stand densities; resistance or tolerance to herbicides alone or in combination; and/or environmental measurements such as soil moisture probes.

Selection of superior genotypes may occur directly, in the case of self-pollinated or inbred lines for example, or indirectly, by allowing the identification of superior progeny (hybrids) thereby allowing the identification of superior parental lines for example. The dataset may establish and maintain a linkage between the planted seed sample and the observations and/or data on a particular plant or assemblage of plants, such as a plot for example. In addition, research locations and plots may be established and maintained in compliance with regulatory requirements and issued permits.

Using geospatial data in research activities may provide advantages such as the use of automation to reduce errors, improving data availability and quality, and/or enabling new processes/technologies for example. In addition, using geospatial data in research activities may allow the data collected for research purposes to be aggregated and utilized in other activities and in other ways. For example, the data collected for research purposes may be aggregated and utilized for seed production purposes, sales and/or marketing purposes, customer use purposes, and/or other non-research purposes. Similarly, data collected in other types of activities may be relevant to analyses performed on data collected for research activities. For example, seed production data, sales and/or marketing data, customer data, and/or other non-research data may be collected from areas surrounding a research area and may be used for a research-related purpose.

III. Seed Production

The seed production aspect of a plant or seed business may engage in activities directed towards producing sufficient quantities of commercial seed for sale. To do so, the seed production organization may grow desired plants in fields owned and/or controlled by the business. Alternatively, the business may contract production fields from others, or potentially even buy grain for use as seed. The process of buying grain from others in this context may also be referred to as sourcing commercial grain.

FIG. 8 provides an example of a tool that may be used for accessing data within an enterprise-wide data set and/or a multi-enterprise-wide data set. FIG. 8 provides a tool that may be used for sourcing commercial grain on an identity preserved basis for augmenting seed supplies for a shortage of seed. A shortage of seed may be caused by a drought, disease, or in cases of unanticipated changes in demand for example. In FIG. 8, a screen display 800 may be provided which may be associated with a web portal or other type of software application. A user may be allowed to specify a hybrid and/or variety using a drop down list box, such as drop down list box 802 for example. The tool may also allow a user to limit results and/or sort results by location. For example, a user may set a current location by using dropdown list box 804 and may set location limitations by using dropdown list box 806. The user may also select the type of sources of interest. For example, the user may indicate that they are interested in crops growing in a field in the current year, crops growing in a field in a previous year, or grain currently in storage 808. A display box 810 may be used to display the data being requested and/or the data being accessed. For example, the display box 810 may show location 812, quantity 814, source 816, and/or type 818, which may be associated with seed or land unit information being requested and/or accessed.

Using a tool for accessing data, such as the tool illustrated in FIG. 8 for example, a user may identify possible sources of seed supplies. Once possible sources of seed supplies are identified, a user may obtain additional information about these sources to assist in making decisions. There may be several different scenarios for use of different sources of seed. For example, seed from commercial grain storage may be appropriate for use, however seed from on-farm storage may be not be appropriate for use. Commercial grain storage data may include a location, an amount, a type, a condition, quality, trait(s), current storage conditions, and/or historical data associated with the commercial grain for example. Another source of seed may include seed being stored in farmer's storage bin for example. Seed may also be produced by the organization, but not needed or used immediately. For example, seed may be produced but released for sale as grain or raised for grain but then desired by the company for use as seed. In the above described embodiments, and any other embodiment described herein, storage location may be a geospatial component and other pieces of data may be linked to the storage location.

Figure 9:
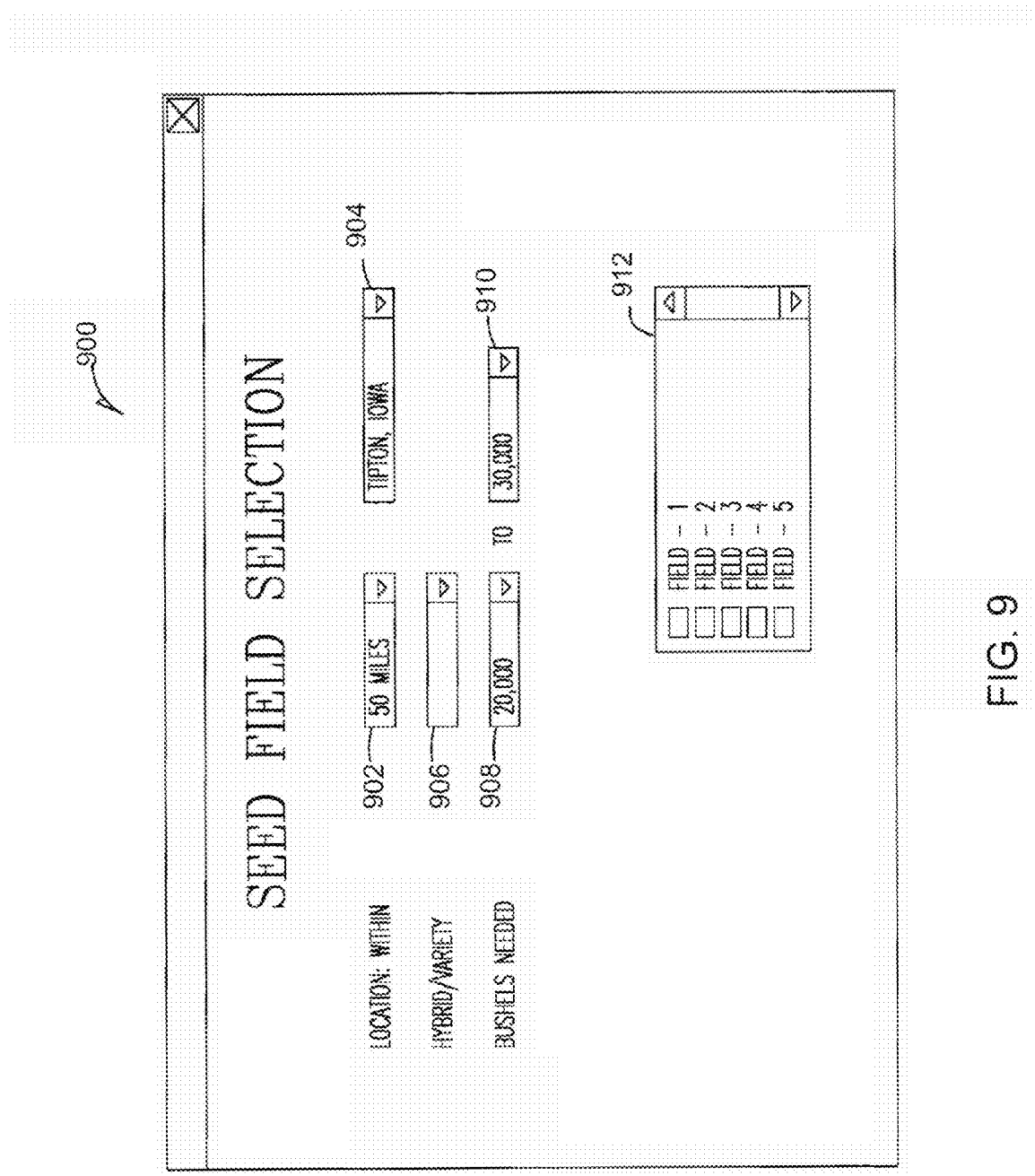
FIG. 9 is a screen display of a tool that can be used for selecting seed fields.

FIG. 9 provides an example of a tool that may be used by a seed company to assist in the selection of seed fields. A screen display 900 may assist in seed field selection. A user may specify the location for seed fields, such as by indicating that the seed fields should be within a certain distance of a particular location for example. The location for seed fields within a certain distance of a given location may be indicated through the use of drop down list box 902 that may specify various distances and drop down list box 904 that may specify various locations. The user may also specify a hybrid or variety to plant using the drop down list box 906, as well as a range of bushels of seed being requested, such as may be specified with input boxes 908 and 910 for example. Fields matching the specified criteria may be displayed in a list box 912. A user may select one or more of the fields within the list box 912 to obtain additional information about the one or more fields of interest.

In addition to the criteria specified by the user, the tool may take into account additional criteria, business logic, and/or business rules in identifying potential seed fields. For example, the tool may receive and/or consider known crop plans in place in adjacent fields, crop histories for a given field or its adjacent fields, risks of disease or pathogen contamination, expected yield in each field, and/or other criteria.

Figure 11:
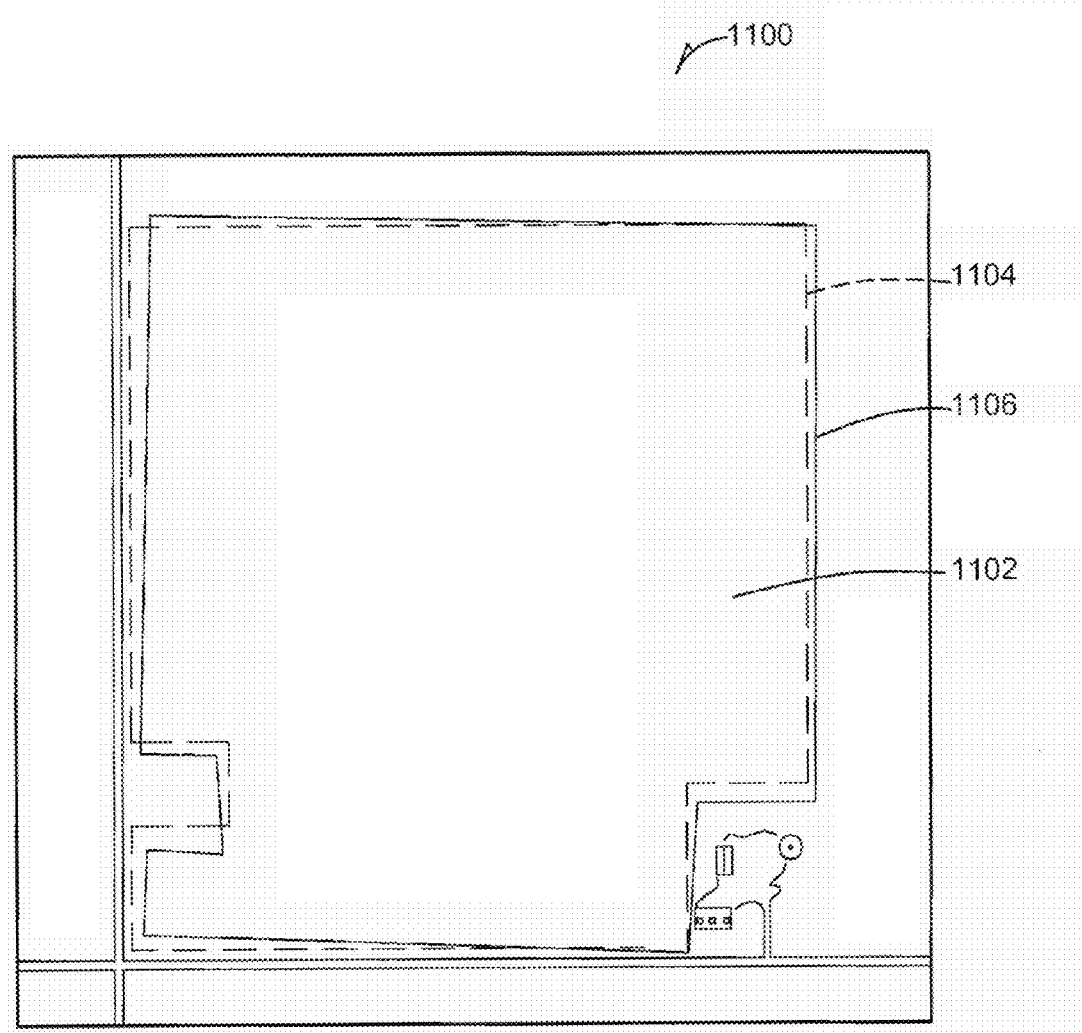
FIG. 11 illustrates a field with two different field boundaries.

FIG. 11 illustrates another example of using geo-referenced data in a manner which may enhance the production process. In FIG. 11, a map 1100 which includes a field 1102 is shown. The field 1102 may be defined by two different boundaries. There may be a first boundary 1106 and a second boundary 1104. The second boundary 1104 may be based on data created by a production location or facility using GPS to collect map data directly in the field. For example, the second boundary 1104 may be created by a production location or facility using GPS data. The GPS data may be collected by precision farming equipment, a GPS-enabled mobile device, such as a cell phone, or another GPS-enabled device. The first boundary 1106 may be created by a production location or facility without the use of GPS data collected directly in the field. For example, the first boundary 1106 may be created using a mouse associated with a personal computer. The mouse may draw the boundary directly over an aerial photograph for example. The first boundary 1106 may be less accurate, but may satisfy business requirements for production of some crops, or types or classes of crops. Business requirements for certain types of production may, however, be different than business requirements for other types of production. For example, business requirements for corn production may be different than business requirements for soybean production. For example, corn seed producers may be compensated, at least partially, based on an area of a field whereas soybean producers may be compensated in a manner which is not dependent upon the area of the field. Similarly, the business requirements for non-transgenic production may differ from the business requirements for transgenic production.

Thus, as shown in FIG. 11, geo-referenced data associated with a field 1102 may be collected at different times and for different purposes. However, if the geo-referenced data is combined in the database, redundant efforts may be avoided and the more accurate data may be used. For example, the second boundary 1104 may be used when aggregated in the same database as the first boundary 1106, as the second boundary 1104 is based on GPS data obtained while in the field.

Figure 12:
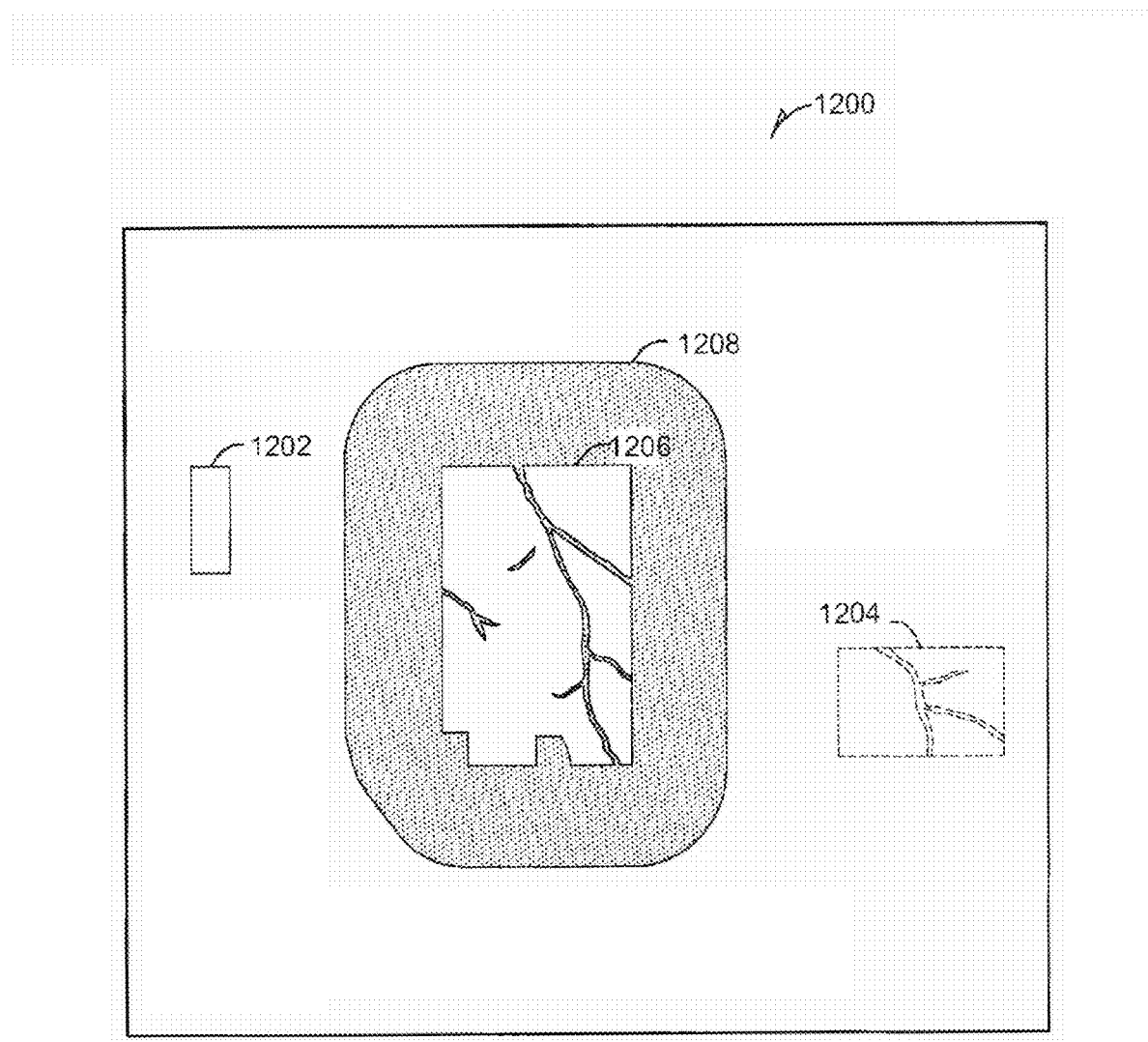
FIG. 12 illustrates a seed production field adequately isolated from a research experiment and a customer's commercial field.
Figure 13:
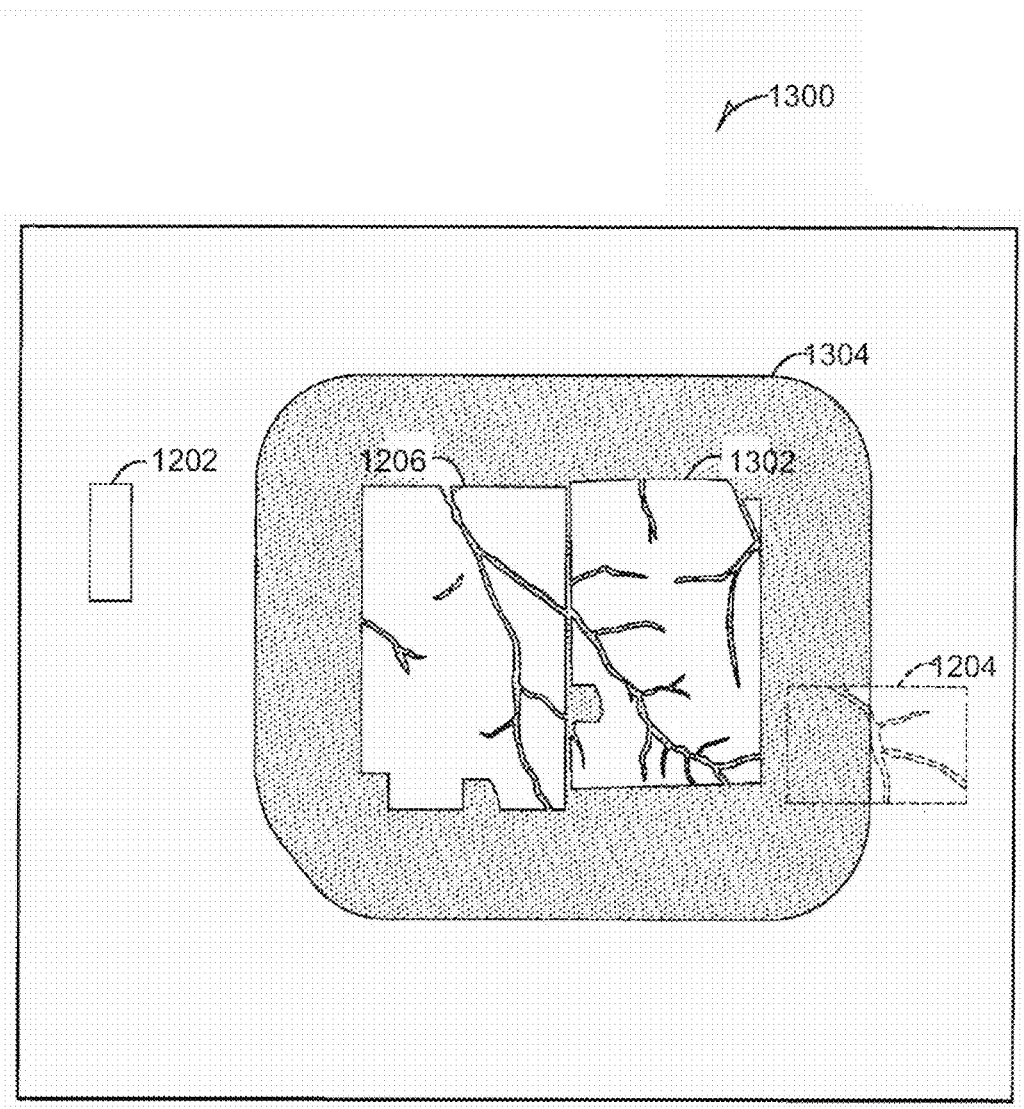
FIG. 13 illustrates a seed production field isolated from a research experiment, but not adequately isolated from a customer's commercial field.

FIG. 12 and FIG. 13 illustrate additional examples where geo-referenced data may be obtained from multiple sources and may be aggregated together. In FIG. 12, a map 1200 is shown. The map 1200 includes geo-referenced data from a research data source, a production data source, and a sales and/or marketing data source. The map 1200 may include geo-referenced data for a research experiment 1202 that may be obtained from a research data source, geo-referenced data for a seed production field 1206 that may be obtained from a production data source, and geo-referenced data for a customer's commercial field 1204 that may be obtained from a sales and/or marketing data source. As shown in FIG. 12, it may be advantageous to aggregate data from all of these data sources and output the aggregated data in the form of map 1200. An isolation zone, such as isolation zone 1208, may surround the seed production field 1206. Knowing the relative location of the research experiment 1202 and the commercial field 1204 may assist a production business organization or group because it may provide greater knowledge concerning the surrounding areas, which may not otherwise be available. This information may be used to better plan, monitor, and/or verify compliance with internal quality or purity standard, safety standards, legal, governmental, regulatory, or other compliance standards, or combinations thereof.

FIG. 13 illustrates a map 1300. The map 1300 includes the research experiment 1202, the commercial field 1204 and the production field 1206 shown in FIG. 12. In addition, there is a second production field 1302 shown in FIG. 13. An isolation zone 1304 is shown which surrounds the adjacent production fields 1206 and 1302. The commercial field 1204 falls within the isolation zone 1304. Because the commercial field 1204 may be too close to the second production field 1302, the second production field 1302 may not be sufficiently isolated and thus the second production field may not be used for production of seed where the isolation zone may be needed and/or preferred.

An individual or group of individuals associated with a production business organization within an enterprise may be able to quickly determine instances where a production field is not properly isolated using the aggregated geo-referenced data described herein. This may provide a significant time savings and increased efficiencies, as well as opportunities to improve and verify metrics on resource utilization, capacity planning, seed quality, seed purity, legal, regulatory, or governmental compliance, or the like.

Some concerns that may be associated with seed production may be addressed as described below. In seed production, there are at least three concerns that are impacted by seed field selection. These concerns may include genetic purity, disease risk or pathogen contamination, and yield. With regard to genetic purity, field selection may have an impact upon the risk of genetic contamination from pollen moving from a nearby field that may contain a contaminating pollen source for example. A risk of genetic contamination may also come from physical contamination from the growth of volunteer plants, such as plants that originate from seed planted in a previous cropping seasons. With regard to disease risk or pathogen contamination, there may be a wide variety of pathogens that may survive in the soil or within previously infected crop residues. In addition, a range of insect, nematode, fungal, viral and/or bacterial plant pathogens may survive from one cropping season to the next in an insect vector for example. For example, the geospatial location of a prior season's disease problems and/or potential insect vector populations may necessitate the use of preventative measures, such as field level quarantines, mandatory fallow periods, and/or prophylactic use of pesticides for example, which may reduce or eliminate insect vectors or protect the crop against infection, such as head smut in corn for example. With regard to yield concerns, the amount of seed produced per unit of land is a function of the number of plants that are planted and survive to contribute to yield, the number of seed produced per plant, and the weight of each seed. Fields may be selected based upon historical yields of commercial crops on either a field basis or more specifically by mapping yield within a field. For example, the yield within a field may be mapped using a yield monitor. In the absence of either historical seed yields or grain yields, historical yields may be estimated by the use of historical satellite imagery, such as that provided by the LandSat satellites for example. In using historical satellite imagery, a biomass index, such as the Normalized Difference Vegetative Index (NDVI) for example may be obtainable for many years and may provide an estimate of biomass accumulation within a field. Thus, areas prone to drought because of low water holding capacity or to flooding may be distinguishable from higher yielding regions of a field or from other potential fields. The percentage of a field with these types of problems may be estimated using yield maps alone or in combination with other inputs such as satellite or aerial imagery and a yield comparison made between regions or fields so that the highest potential yielding fields or regions with a permanent field may be selected.

Of course, yield is not known in advance, but projections may be made. In any specific field and production year there may be significant variation in yield. By accruing yield data, climatic or weather data, and imagery of the crop over time it may be possible to develop a yield stability measure for areas within a field, fields, and/or production regions. This may permit not only the selection of areas with the most stable seed yields, such as the seed yields that are the most consistent over time for example, but also the development of risk management factors. Risk management factors may be used to adjust production acreages according to an assessment of risk factors that may include long range weather forecasts, soil profile moisture availability at the start of the production season, existing inventory levels, availability of irrigation, genotype specific characteristics such as drought tolerance, or the like.

Using geospatial data in seed production activities may allow the data collected for seed production purposes to be utilized in other activities and in other ways. For example, the data collected for seed production purposes may be utilized for research purposes, sales and marketing purposes, customer use purposes, and/or other non-production purposes. Similarly, data collected in non-production types of activities, may be relevant to analyses performed on data collected for seed production activities.

Thus, use of an enterprise-wide data set and/or a multi-enterprise-wide data set may be advantageous in the seed production aspect of a seed or plant sciences business. It is to be understood that what is discussed here is merely representative of the ways in which such data may be used to provide advantages or efficiencies.

IV. Sales and/or Marketing

The sales and/or marketing aspect of such a business may provide for selling the seed. A number of activities may support that goal. The activities may include providing associated services to producers which may help the producers select which seed products to use and/or related agronomic services which make recommendations regarding product placement or management practices which may be used with the seed products. Agronomic services may include such services as ag-chemical sales, crop insurance, crop modeling, and/or grain merchandising for example. In addition, activities may assist producers in selling their resulting crops which may be grown from the seed products.

To assist in the sales and/or marketing aspect of a business, it may be advantageous to know as much about a particular field or land unit as possible. By accruing yield data, climatic or weather data, and/or imagery of the crop over time it may be possible to develop better recommendations for a particular land unit or field. The same field may be used for different purposes over time. For example, a single producer field may be used to grow different types of crops. As an example, corn may be grown in a field in one year and soybeans in a different year. Additionally, a single field may be contracted for production use in one year and not in another year for example. Thus, various types of information may be available from different aspects of a seed or plant science company to assist in making recommendations for a future crop.

In addition, the sales and/or marketing aspect of a business may be in a position to collect data from producers regarding seed products. For example, data from producers may include the particular seed product planted in a field, as-planted data, harvest data, management practices data, or other data related to crop production activities or crop performance. This data may be of potential value to other aspects of the business as explained in various examples as provided herein.

Additionally, as the aggregation of data may provide advantages to the seed company or life sciences business, direct advantages may also be created for the producer. For example, if a seed company customer leverages an online service for record keeping and managing their business, then information contained in the seed company's records may create new marketing opportunities for the seed company and advantages for the seed company's customers or producers. As an example, if a customer purchases a new soybean variety and stores production of this variety in a grain bin, the grain may be valuable as a source of identity preserved grain which may be used as seed if soybean seed supplies become inadequate to meet demand. In the absence of an enterprise-wide database or other linking of the production and sales organizations, then the process of identifying customers who purchased a particular product and who have grain in storage may be dependent upon numerous phone calls. Any organization within the company may query a database for all customers who purchased and/or planted a specific seed variety for example. The farm records entered by the customer may provide, if permission were granted, a means to locate supplies in a specific quantity and/or geographic region. The producers identified may benefit in the potential for increased profits for sale of their crop as seed as opposed to as commodity grain.

The database may also be accessed when a farmer plants a known product adjacent to a seed field, or within a specified zone around the field, as this information may become populated in a data layer that may describe current cropping information. Thus, seed production personnel may not need to make subsequent inquiries about the identity of a product within a nearby field if its identity was already known. For example, a producer may enter information into an on-line farm management tool or the planting history for a land unit may be entered by a sales representative working with a seed company.

In addition, the use of aggregated data may allow local or regional end users to be linked with grain producers and/or production plants. For example, if demand exists for corn in a region, the end user may access a marketing system that may link producers who may have grain in storage with grain consumers. The system may create value for the grain consumer by identifying locations, volumes, hybrid or variety products, and quality. This linkage between a farmer's records, geospatial data on storage facilities, and grain/seed sampling abilities may facilitate mutually beneficial transactions by efficiently linking producers and consumers. For seed companies or other entities, this may create an additional aspect to the seed customer and seed company relationship that may help the customer extract greater value from their investment in seed from the seed company.

Thus, sales and/or marketing may provide a source of data that may be used for other purposes. For example, the data collected for sales and/or marketing purposes may be utilized for research purposes, seed production purposes, customer use purposes, or other purposes. Additionally, sales and/or marketing producers or customers may benefit from the use of the data collected elsewhere throughout the business or from another business.

V. Further Applications and Examples

Figure 7:
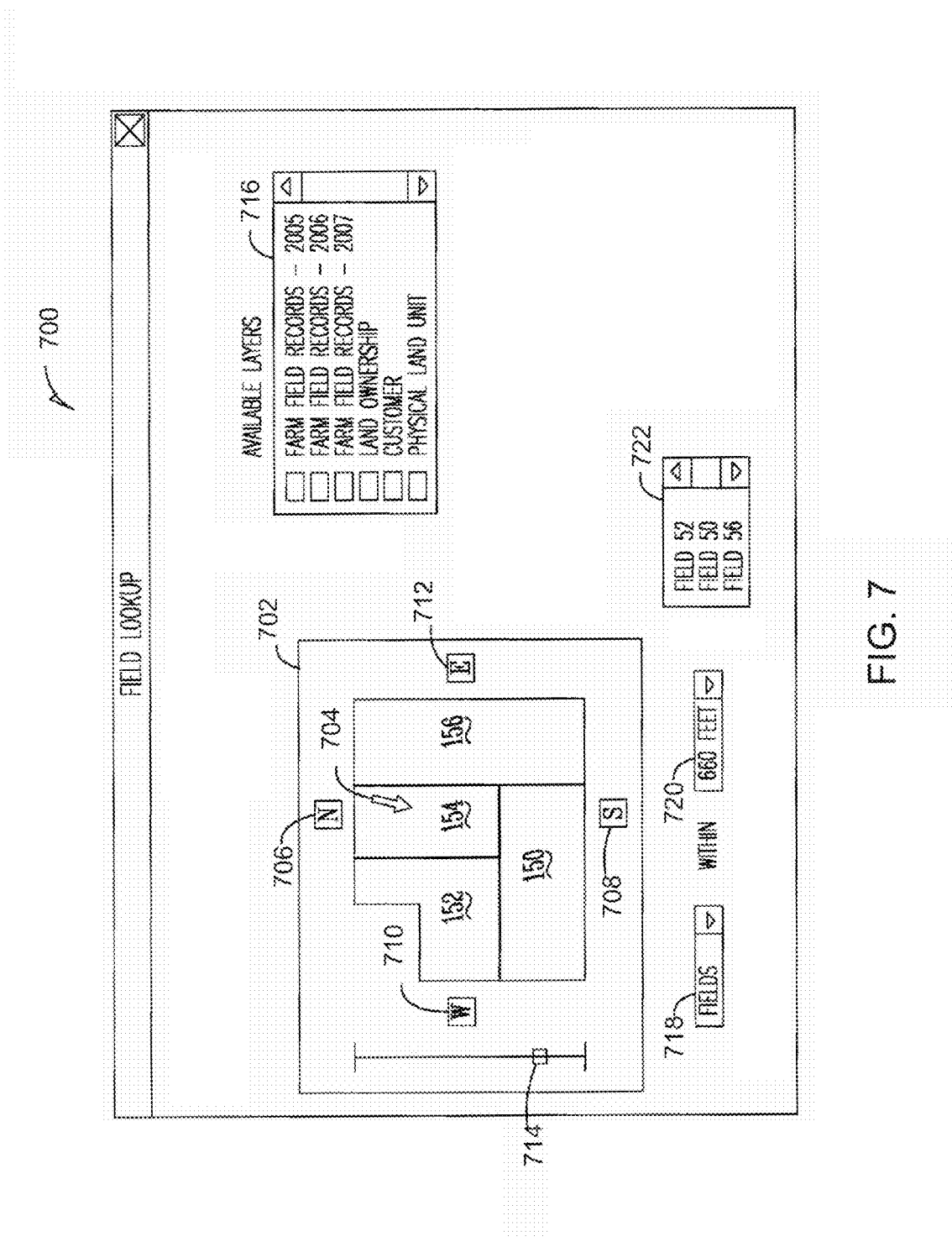
FIG. 7 is a screen display of a look-up tool that may be used to access geo-referenced data.

In addition to the tools described which may be used for more specific applications for particular aspects of a business, general purpose tools may also be used. FIG. 7 provides a screen display of one example of a look-up tool that may be used to assist in making decisions based on available data associated with a field. A window 700 may include a map region 702 which may display a map that includes fields 150, 152, 154, and 156. The map region 702 may include controls which allow for scrolling north 706, south 708, west 710, east 712, as well as a sliding zoom control 714. Other types of map controls may be used. The map shown may be based on aerial imagery, satellite imagery, digital elevation models, or other types of maps, or may be switchable between types of maps, or combinations or overlays of more than one type of map for example. A user of the look-up tool may select a land unit. For example the user may use a mouse cursor in the form of an arrow, such as arrow 704 for example, to select a field. Upon the mouse being placed over the field 154, available data layers for the field may be shown in list box 716. The available data layers may include geo-referenced data which may be geo-referenced to any position within the field. In addition, where data changes on a periodic basis multiple layers may be presented. For example, farm field records for each available year may be presented as items in the list of available layers. A user may select one or more of the available layers to display corresponding information over the field where appropriate.

The tool may also provide for identifying other fields, objects, or points of interest which may be adjacent, or near a selected field. An object may be defined by boundaries or an object may be defined as a group of data points for example. Examples of other objects or points of interest may include, without limitation, seed and grain storage facilities, seed production distribution points, transportation infrastructure data points, and/or grain utilization points. A dropdown list box 718 may allow a user to select whether they are searching for fields or other points of interest. Another drop down list box 720 may allow a user to select a range of interest. For example, the range of interest may be within 660 feet, as illustrated in FIG. 7, which may be a commonly accepted isolation distance to prevent cross-pollination. The range of interest may also specify adjacent or nearest fields or points or objects of interest. Based on the selections made in dropdown list box 718 and dropdown list box 720, a list box 722 may be populated with fields or other objects or points of interest which meet the defined criteria.

Geospatial data in agriculture may be linked or keyed to a common land unit (CLU), a concept developed by USDA. For an agricultural company, the CLU boundaries created by the USDA or other similar agencies in other countries may not be entirely applicable for its needs because those boundaries may include areas within fields that may not be croppable, but may be of interest to the government agency. The CLU designations or something similar, when available, may be valuable referents for use by external information providers or by farmer/cooperators and may represent a generally recognized geospatial context for example.

The enterprise-wide geospatial database may include the CLU data or its equivalent. The enterprise-wide database need not be a single database but may be a collection of one or more data stores. However, the primary geographic entities may be referred to as "permanent fields." A permanent field may be an object defined by its boundaries which persist over time; it may not be affected by ownership, cropping patterns or other ephemeral conditions. Distinct regions within a permanent field that are currently being utilized for some enterprise function such as seed production may be referred to as "current fields." Current fields may be subsets of the area within a permanent field. For example, each permanent field may contain one or more current fields, with each current field containing a unique product based upon its genetic makeup, planting date, and/or isolation class. "Permanent fields" may provide one way of linking data, whether seed production data or crop production data, which may be obtained from different sources and/or for different periods of time. In addition, the enterprise-wide geospatial database may be indexed by permanent field.

The tool shown in FIG. 7 illustrating permanent fields may be one way in which data may be combined from different data sources. The tool may allow a user to observe relationships between data in order to support various decision making processes and otherwise facilitate business functions and/or processes. The tool shown in FIG. 7 may be made available over a network, through a web portal, or otherwise. It may also be appreciated that the data sources may be combined based on user-defined rules, business logic, or through the use of various algorithms that may be used to find relationships between data that may be relevant to a decision to be made. Thus, data collected for one purpose may have value when used for another purpose. Similarly, data which may traditionally have been considered to be not relevant or marginally relevant to a particular decision may be used to better inform the decision.

The tools illustrated in FIG. 7 through FIG. 9 are merely representative of the tools that may be used to access data for particular purposes. In all of these tools, additional criteria, business logic, and/or business rules may be used in addition to search criteria specified by a user. In addition to these tools, expert systems or optimization algorithms may be used instead or in addition to these types of query-driven systems for example. The expert systems or optimization algorithms may allow for more complex types of analysis as may be appropriate in particular situations. Thus, the availability of the data in aggregate form may provide opportunities for querying, optimizing, and/or reporting that may not otherwise be available without the underlying data from different data sources.

Figure 10:
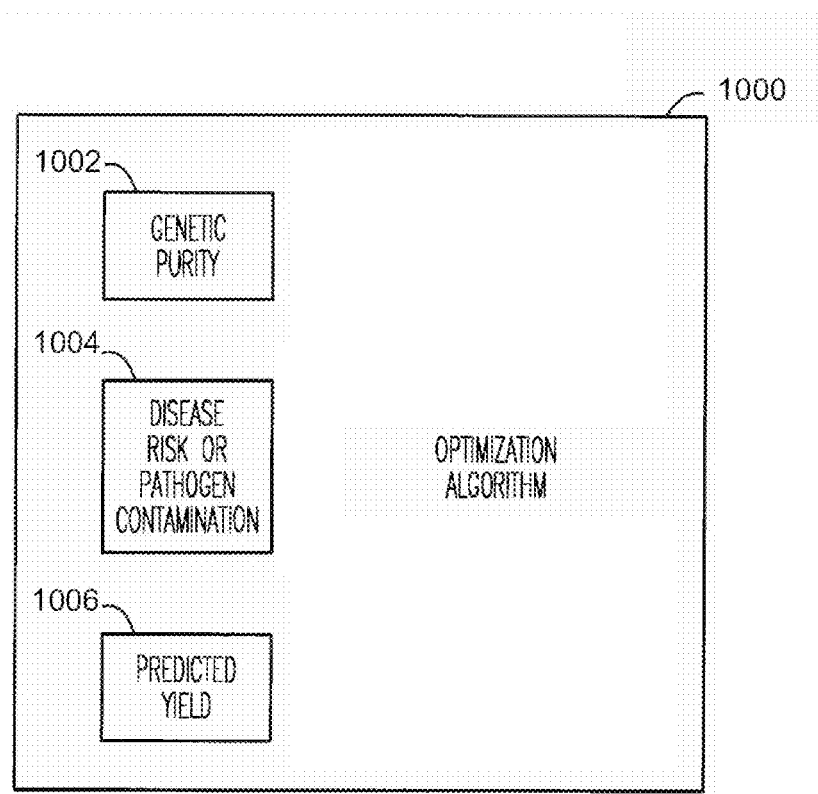
FIG. 10 is a block diagram of an optimization algorithm.

The aggregation of data from various data sources may also allow for opportunities for data analysis for optimizations and other objectives. For example, FIG. 10 illustrates one example of an optimization algorithm 1000. The optimization algorithm shown here uses genetic purity 1002, disease risk or pathogen contamination 1004, and predicted yield 1006 to assist in finding optimum field locations. In addition to these types of constraints or parameters, other constraints or parameters may be used, including geographical constraints. The optimization algorithm 1000 may be of various types including evolutionary algorithms, genetic algorithms, linear programming algorithms, mixed-integer linear programming algorithms, fuzzy logic algorithms, or any number of other types of optimization algorithms, or combinations of these and other algorithms. The optimization algorithm 1000 may be used for optimization where there are competing objectives.

The geo-referenced data contained in the database may be used for any number of purposes, whether accessed using search criteria, a query formulated by a user, and/or directly accessed by an optimization algorithm to provide a solution to a problem.

Thus, the geo-referenced data from the different data sources may be aggregated to provide increased efficiencies and/or provide the data useful for additional types of analysis. Examples of ways in which the geo-referenced data may be used may include, without limitation:

1. Optimizing seed field selection across multiple production facilities, fields and products for the purposes of maximizing seed yield, isolation from contaminating pollen sources such as transgene and/or pure seed crops for example, minimizing transportation costs, accessing irrigation, minimizing risk, leveraging labor and/or harvest equipment availability.
2. Sourcing commercial grain, on an identity preserved basis, for augmenting seed supplies in the event of a shortage of seed because of drought or disease or in case of unanticipated changes in demand.
3. Selecting stored seed to minimize transportation cost by applying an algorithm that may factor in the conversion rate of unfinished seed into product suitable for sale and the distance from the storage location to the production plant. Factors may include demand by product and/or quality of seed in bin.
4. In the field selection and planning processes which may occur across many independent production facilities, production plans may be integrated across multiple product lines, such as corn and soybean for example, to allow contracts to be written for seed corn production fields with seed beans used to provide isolation from contaminating pollen sources.
5. Optimizing merchandizing plans for selling excess or below quality seed production for use as grain.
6. Adjusting seed grower compensation by accurately calculating local basis prices and/or transportation costs that would impact the value of a seed producer's crop when expressed in grain equivalents.
7. Providing regulatory oversight and/or business rule enforcement that may monitor the placement of commercial demonstration plots and/or research plots during the planning process, to avoid contamination of research, testing, development, demonstration, or seed production blocks.
8. Providing genetic element or genotype tracking so that the location of all research, sales, marketing, regulatory, or production blocks may be known as well as the specific lot or lots of seed that may be used in the planting process. The coordinates of each plot may be defined so that as-planted plot maps may be generated. This tracking may allow any specific plot, such as plots planted with a lot of concern for example, to be located and/or any adjacent plots to be identified if a regulatory issue or concern may arise that may require tissue sampling for determination of contamination or crop destruction.
9. Tracking and recording significant weather data over time on a field by field basis, then using that data to predict crop maturity and performance. Weather data may also be used for providing an explanation for why seed yields that were observed may have occurred. In other words it may be possible to normalize yields by year so that relative yield potential of a field may be explained. However, if a comparison is made between fields that are separated by some distance then it may be important to have data records by field because localized weather events may have an impact on the ultimate yield of a field. For example, weather events such as hail or rainfall may be very narrowly localized.

10. Optimizing resource use based on various needs across the business and/or functions. For example, a corn variety having specific isolation requirements can be planted within defined field boundaries, geographic location, transportation access, and the like, and surrounding available land can be planted with an second crop, such as soybean, the fully utilize the arable land, while maintaining the required isolation and other criteria needed for the corn variety.

The geospatial database may serve as the common basis or platform for exchanging plans for where plots may be planted and for responding to potential issues during the growing season.

The database may also allow different functions or groups to work more efficiently. For example, it may be possible to have soybean seed production staff map a field for their use without knowing that its boundary has already been mapped by a neighboring corn production plant for its use in alternate years. The database may define unique pieces of land in a uniform manner so that the business has an accurate and agreed upon definition of a land unit. Current and historic information about that land unit, as well as future plans for its use, could be readily shared among all organizations or divisions within the company.

In another example, in the absence of the enterprise-wide geospatial database or proper linkage between disparate data sources and the ability to facilitate cooperation and compliance with business rules, it may be possible for a seed salesperson to unknowingly encourage a customer to plant a trial plot of a genetically modified organism (GMO) product in an undesirable location. For example, if improperly placed in close proximity to a seed field, the planting by a customer of the GMO product in an undesirable location may become a source of contaminating pollen to the seed field.

Data from different data sources or data collected for different purposes may be relevant to making decisions. A database which includes geospatial data may allow efficient use of data or information across functions of an entity. Using geospatial data as a linkage may provide a geographical context within which non-geospatial data may have a context or relevance.

In an organization such as an agriculture or life sciences company, there may be a vast amount of data collected or generated by diverse business units for diverse purposes. Where data may be associated with geospatial information, the data may have increased value when used for purposes other than the purpose for which the data was originally collected. For example, research data, production data, and/or sales or marketing data may be combined where geospatial data may be used to link such diverse data sets.

Therefore, methods and systems for use of geospatial data have been disclosed. Numerous variations, options, and alternatives are contemplated.

What is claimed is:

1. A system comprising:
   a processor; and
   computing memory having stored therein instructions that when executed by the processor perform the following:
   receiving seed product development data from a seed product development source, wherein the seed product development data comprise geospatial information associated with at least one of a seed product or a land unit used for seed product development;
   receiving seed production data from a seed production source, wherein the seed production data comprise geospatial information associated with at least one of a seed product or a land unit used for seed production;
   receiving seed sales and marketing data from a seed sales and marketing source, wherein the seed sales and marketing data comprises geospatial information associated with at least one of a seed product or a land unit used for seed sales and marketing;
   receiving governmental or regulatory requirements associated with a seed product; and
   developing, at the processor, a planting plan, in response to a query and based on aggregating the seed sales and marketing data with the seed product development data, the see production data, and the governmental or regulatory requirements based on the respective geospatial information.

2. The system of claim 1 further comprising:
   receiving agronomic services data from an agronomic services source, wherein the agronomic services data comprises geospatial information associated with at least one of a seed product or a land unit used for agronomic services; and
   aggregating the agronomic services data with the seed sales and marketing data, the seed product development data, and the seed production data based on the governmental or regulatory requirements based on the respective geospatial information.

3. The system of claim 2 wherein the agronomic services further comprise at least one of ag-chemical sales, crop insurance, crop modeling, or grain merchandising.

4. The system of claim 1 wherein the geospatial data defines field boundaries.

5. The system of claim 1 wherein the geospatial data further comprises data points associated with a land unit based on the geospatial position of a data recorder and the land unit.

6. The system of claim 1 wherein the query is adapted to request information relevant to at least one of plant research, seed production, sales and marketing, grain sourcing, a merchandising plan for selling excess seed production for use as a grain, a merchandising plan for selling below seed production quality seed for use as grain, seed grower compensation, placement of plots, seed sourcing from stored grain, or genetic purity of a crop or seed grown in a plot.

7. The system of claim 1 wherein the query is adapted to apply an optimization algorithm to the seed product development data and the seed production data.

8. The system of claim 7 wherein the optimization algorithm is an evolutionary algorithm, a genetic algorithm, a linear programming algorithm, or a mixed integer linear program algorithm.

9. The system of claim 7 wherein the optimization algorithm uses at least one of genetic purity information, disease risk or pathogen contamination information, or predicted yield information to assist in finding an optimum land unit location.

10. The system of claim 7 wherein the output data comprises at least one of physical land unit data, cropping history data, land ownership data, seed grower data, seed storage data, grain storage data, seed facility data, grain facility data, seed production distribution point data, transportation infrastructure data, grain utilization point data, current crop data, or field entrance data.

11. The system of claim 1 wherein as a result of the query, the seed product development data is usable for seed product development purposes.

12. The system of claim 1 wherein the aggregating step further comprises aggregating the seed product development data and the seed production data, and the governmental or regulatory requirements based on at least one of a user-defined rule or business logic.

13. The system of claim 1 wherein the seed product development data and the seed production data, and the governmental or regulatory requirements are aggregated in a database.

14. The system of claim 1 wherein any one of the seed product development data or the seed production data is received from a local source and the other of the seed product development data or the seed production data is received from a remote source.

15. The system of claim 1 wherein the seed product development data indicates a transgenic seed in development associated with a first land unit, wherein the seed production data indicates a seed in production associated with a second land unit, and wherein the output data indicates a potential interaction between the transgenic seed and the seed in production.

16. A method comprising:
receiving seed product development data from a seed product development source, wherein the seed product development data comprises geospatial information associated with at least one of a seed product or a land unit used for seed product development;
receiving seed production data from a seed production source, wherein the seed production data comprises geospatial information associated with at least one of a seed product or a land unit used for seed production;
receiving seed sales and marketing data from a seed sales and marketing source wherein the seed sales and marketing data comprises geospatial information associated with at least one of a seed product or a land unit used for seed sales and marketing;
receiving governmental or regulatory requirements associated with a seed product;
and
developing, at the processor, a planting plan, in response to a query and based on aggregating the seed sales and marketing data with the seed product development data, and the seed production data, and the governmental or regulatory requirements based on the respective geospatial information.

17. The method of claim 16 further comprising:
receiving customer data from a customer source, wherein the customer data comprises geospatial information associated with a customer;
aggregating the customer data with the seed sales and marketing data, the seed product development data, and the seed production data, and the governmental or regulatory requirements based on the respective geospatial information.

18. The method of claim 16 wherein the query is adapted to request information relevant to at least one of plant research, seed production, sales and marketing, grain sourcing, a merchandising plan for selling excess seed production for use as a grain, a merchandising plan for selling below seed production quality seed for use as grain, seed grower compensation, placement of plots, seed sourcing from stored grain, or genetic purity of a crop or seed grown in a plot.

19. The method of claim 16 further comprising sending output data in response to a query and based on said aggregating, wherein the output data comprises at least one of physical land unit data, cropping history data, land ownership data, seed grower data, seed storage data, grain storage data, seed facility data, grain facility data, seed production distribution point data, transportation infrastructure data, grain utilization point data, current crop data, or field entrance data.

20. The method of claim 16 wherein the geospatial data defines permanent field boundaries.

21. The method of claim 16 wherein the query is adapted to request seed sourcing information, wherein the seed sourcing information comprises geospatial information associated with stored commercial grain.

22. The method of claim 16 wherein the query is adapted to apply an optimization algorithm to the seed product development data and the seed production data.

23. The method of claim 22 wherein the optimization algorithm is from a set consisting of an evolutionary algorithm, a genetic algorithm, a linear programming algorithm, and a mixed integer linear programming algorithm.

* * * * *

UNITED STATES PATENT AND TRADEMARK OFFICE
CERTIFICATE OF CORRECTION

| | | |
|---|---|---|
| PATENT NO. | : 8,862,630 B2 | Page 1 of 1 |
| APPLICATION NO. | : 12/793437 | |
| DATED | : October 14, 2014 | |
| INVENTOR(S) | : Hunter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 415 days.

Signed and Sealed this
Fifteenth Day of September, 2015

Michelle K. Lee
*Director of the United States Patent and Trademark Office*